United States Patent [19]

Osaki et al.

[11] Patent Number: 4,685,569
[45] Date of Patent: Aug. 11, 1987

[54] METHOD OF DETECTING AND SORTING PIECES OF INSULATING MATERIALS ADMIXED IN SMALL PIECES OF CONDUCTIVE MATERIALS

[75] Inventors: Shigeyoshi Osaki, Takarazuka; Shin-ichi Nagata, Matsubara, both of Japan

[73] Assignee: Kanzaki Paper Mfg. Co., Ltd., Tokyo, Japan

[21] Appl. No.: 662,419

[22] Filed: Sep. 17, 1984

[30] Foreign Application Priority Data

Jan. 18, 1983 [WO] PCT Int'l Appl. ... PCT/JP83/00016

[51] Int. Cl.$^4$ ............................................. B07C 5/344
[52] U.S. Cl. ................................... 209/571; 209/548; 209/559; 209/656; 209/933; 324/455
[58] Field of Search ...................... 209/3.1, 44.1, 3, 4, 209/9, 548, 549, 559, 563, 564, 571, 656, 657, 706, 925, 933, 127 R, 127 B, 131, 932, 44.2; 324/455, 454, 452, 457, 464; 73/863.54, 863.91; 15/316 R

[56] References Cited

U.S. PATENT DOCUMENTS

| 2,587,686 | 3/1952 | Berry | 209/571 |
|---|---|---|---|
| 2,927,690 | 3/1960 | Malmqvist et al. | 209/571 |
| 3,179,248 | 4/1965 | Marley | 209/3.1 |
| 3,710,938 | 1/1973 | Scherf | 209/571 |
| 3,735,641 | 5/1973 | Bink et al. | 73/863.54 |
| 3,933,249 | 1/1976 | Welsh et al. | 209/932 |
| 3,944,076 | 3/1976 | Goulds et al. | 209/571 |
| 3,970,546 | 7/1976 | Webb et al. | 209/3 |
| 4,119,206 | 10/1978 | Woodman, Jr. et al. | 209/548 |
| 4,233,562 | 11/1980 | Blythe | 324/455 |
| 4,299,693 | 11/1981 | Paulson | 209/3 |
| 4,323,159 | 4/1982 | Wolf | 209/548 |
| 4,364,147 | 12/1982 | Biedermann et al. | 15/316 R |

FOREIGN PATENT DOCUMENTS

| 46-12440 | 3/1971 | Japan . | |
| 51-80356 | 7/1976 | Japan . | |
| 52-18374 | 2/1977 | Japan . | |
| 0659189 | 4/1979 | U.S.S.R. | 209/571 |

Primary Examiner—Robert B. Reeves
Assistant Examiner—Donald T. Hajec

[57] ABSTRACT

A method of detecting and sorting pieces of insulating materials admixed in small pieces of conductive materials, which comprises detecting and amplifying the surface potentials of the conductive materials and the insulating materials by a surface potentiometer on the basis of a time differentiation method, inputting the signal to a comparator, and sensing the presence of the insulating materials. This method is utilized to detect and sort plastics admixed in pulp and papermaking materials or cereals.

9 Claims, 8 Drawing Figures

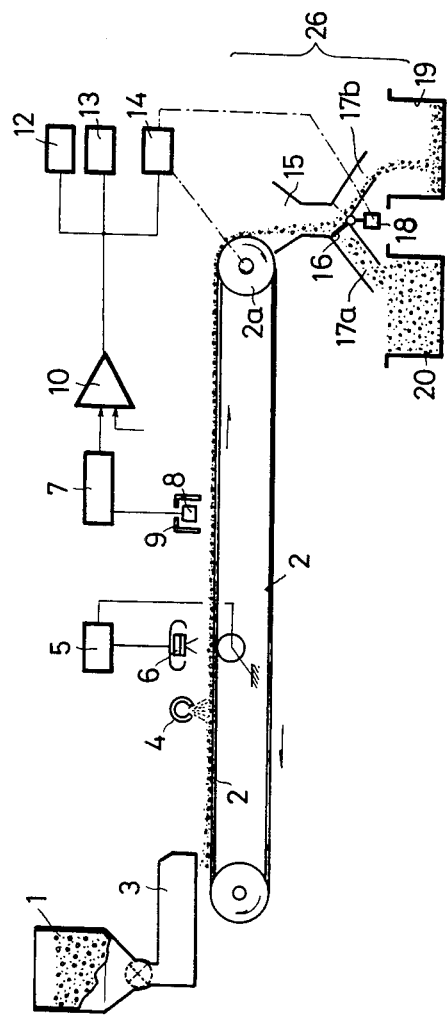
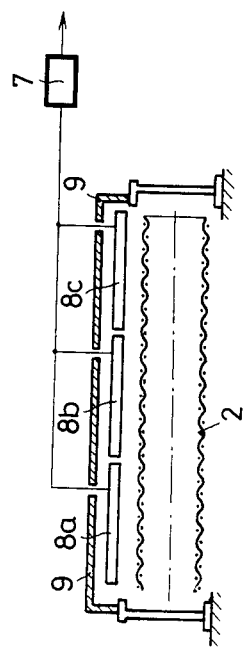
FIG.1
FIG.2

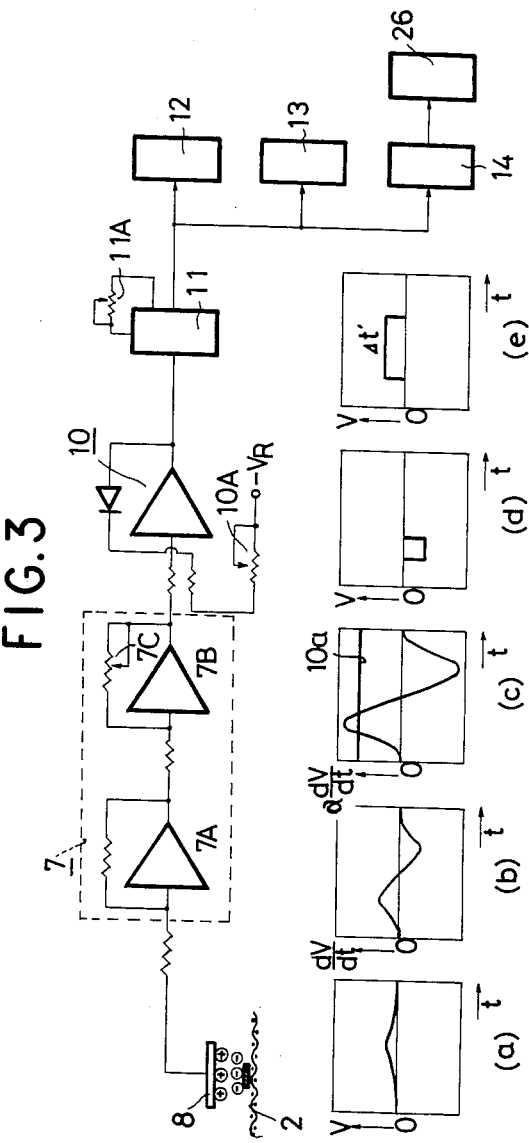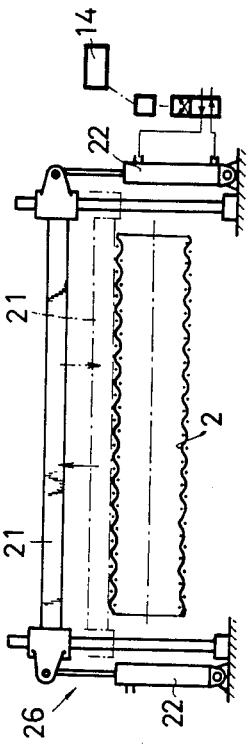

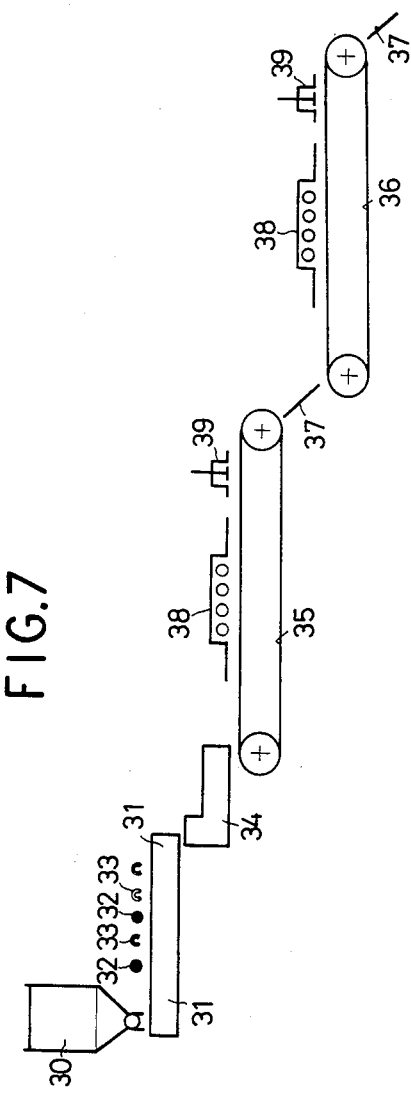

METHOD OF DETECTING AND SORTING PIECES OF INSULATING MATERIALS ADMIXED IN SMALL PIECES OF CONDUCTIVE MATERIALS

TECHNICAL FIELD

This invention relates to a method of detecting and sorting pieces of insulating materials such as plastic or rubber pieces admixed in small pieces of conductive materials such as pulp and papermaking materials, e.g., wood chips or cereals, e.g., soybeans. More particularly, the invention relates to a method of electrically detecting plastic or rubber pieces admixed in pulp and papermaking materials or cereals by the utilization of the difference in electrostatic properties between the conductive materials and the insulating materials, and manually or automatically removing the plastic or rubber pieces from the pulp and papermaking materials or cereals.

BACKGROUND ART

Recently, plastic products have been widely used in various fields, and their utilities have a trend to increase. On the other hand, small pieces of waste plastic products become admixed in pulp and paper stuff or cereals and have accordingly caused a hindrance to processing the pulp and paper stuff or cereals. For example, if small pieces of plastic bags, braids, bands, tags, name plates, receptacles, toys or other plastic or rubber products (which will be hereinafter called "plastics") are admixed in wood chips and such wood chips are pulped as they are, the plastics will be contained in a paper web layer, with the result that pores are formed in the web layer or the web layer is easy to break. Such troubles will occur also when the plastics are admixed in straw, bagasse, hemp, rag, cotton, linter, or waste paper of non-wood pulp and papermaking materials.

Since the plastics are in general chemically stable, the plastics are subjected only to thermal deformation even in a liquor treatment at a high temperature and pressure in a pulping step. As the plastics are further pulverized into fine pieces by mechanical action of a beater, it is extremely difficult to remove the plastics from a pulp slurry by means of a screen of conventional type. As the difference in the specific gravity between the pulps and the plastics is slight, the plastics removal efficiency is low for the large power consumed by a cleaner which utilizes a centrifugal force. Consequently, when the plastics are admixed in the pulp and papermaking materials, it is preferred to remove the plastics in advance. When the plastics are admixed in cereals such as soybeans, it is preferable to remove the plastics before processing because the cereals are used for food.

However, there exist no effective means at present for removing plastics admixed in the pulp and papermaking materials or cereals, and at present the plastics dispersed in the pulp and papermaking materials or cereals are found visually and removed manually.

DISCLOSURE OF THE INVENTION

The present invention provides a method of electrically detecting plastics admixed in pulp and papermaking materials or cereals and a method of removing the plastics therefrom by rejecting means operating in response to the detection signal in the previous method.

The plastics are in general electrical insulators, while pulp and papermaking materials such as wood chips, straw, bagasse, hemp, rag, cotton, linter or waste paper or cereals such as soybeans has a high electrical conductivity as compared with the plastics. Therefore, it is normal that a considerable difference is produced in surface potentials generated by the friction between the plastics and the pulp and papermaking materials or cereals owing to several times of re-stacking or conveyance in the steps of stocking prior to processing and the surface potential difference is further increased by positively applying a corona discharge.

For example, the surface potentials of the plastics admixed in wood chips which have been stored in the open-air and those of the plastics admixed in wood chips which have been conveyed by a conveyor are listed in Table 1 below.

TABLE 1

| Plastics | Surface potential open-air storage | Surface potential* conveyed |
|---|---|---|
| Polyethylene bag | −70 volts | −100 volts |
| Polypropylene plate | −200 | −300 |
| Polytetrafluoroethylene | −100 | −200 |
| Carbon-containing rubber plate | −50 | −100 |
| Polycarbonate film | −100 | −200 |
| Polystyrene film | −200 | −300 |
| Foamed styrene | −50 | −80 |
| Vinyl chloride tape | −70 | −100 |
| Nylon rope | −50 | −100 |
| Sponge | +50 | +100 |
| Wood chips | −0 | −0 |

*The belt conveyor used had a belt 600 mm wide, a conveyance speed of 20 m/min and a conveyance distance of 10 m. The surface potentials of the plastics on the belt conveyor were measured by means of a surface potentiometer, the electrodes of which were disposed 3 cm away from the conveyor. (When a screw conveyor is used, the potential differences will be still larger because of larger friction.)

Table 2 shows the surface potentials of the plastics admixed in pulp and papermaking materials being conveyed on a conveyor, the measurements thereof being made by means of a surface potentiometer having electrodes disposed 2 cm away from the conveyor when a corona discharge was applied for 3 seconds at an applied voltage of 6 KV by a discharging bar disposed at a height of 2 cm above the conveyor.

TABLE 2

| Plastics | Surface potentials |
|---|---|
| Polyethylene bag | −300 volts |
| Polypropylene | −1000 |
| Polytetrafluoroethylene | −3000 |
| Carbon-containing rubber plate | −1000 |
| Polycarbonate film | −1000 |
| Polystyrene film | −1000 |
| Wood chips & non-wood pulp and papermaking materials | −0 |

It was confirmed that high surface potentials were obtained by the corona discharge even when wood chips admixed with plastics contained much moisture, particularly when the chips are treated in advance by steam so as to prevent the chips from igniting due to the corona discharge, and hence the plastics were moistened.

Tables 1 and 2 show the surface potentials of the plastics admixed in pulp and papermaking materials, and the surface potentials of the plastics admixed in cereals such as soybeans were substantially the same as in Tables 1 and 2. As evidently seen from Tables 1 and 2, the conductive pulp and papermaking materials or cereals are not charged even if a corona discharge is applied, while the plastics, being nonconductive, are already charged at the time when the plastics are admixed in the pulp and papermaking materials and, the amount of charge is increased by the friction at the time of conveyance and further increased by the corona discharge.

The present invention relates to electrically detecting the plastics admixed in pulp and papermaking materials or cereals by utilizing the electrical properties of the plastics as described above and to removing manually or by rejecting means to be described later, the plastics from the pulp and papermaking materials or cereals.

More particularly, a method of the present invention comprises the steps of distributing and moving pulp and papermaking materials or cereals admixed with plastics on a relatively flat conveying surface such as a belt conveyor, measuring the surface potentials of the plastics mixed in wood chips or the like or a cereal by means of a surface potentiometer disposed above the conveying surface, the electrodes of said surface potentiometer having an amplifier circuit of a time differentiating method, inputting the time differentiated value to a comparator, sending the output of the comparator to an indicator such as a lamp or an alarm unit as required and also to a timer, and stopping the belt conveyor or operating a means for rejecting the plastics by means of the output signal of the timer delivered after the lapse of the set time thereof.

Specific means for sorting and removing the plastics in the wood chips by the method of the invention will now be generally described.

(1) The output of a surface potentiometer amplified by an amplifier of a time differentiating method is applied to a comparator, and the output signal of the comparator is applied to an indicator such as an alarm unit. When the amplified output of the surface potential collected by the potentiometer exceeds a reference value set in the comparator, the comparator produces a signal, thereby turning on the lamp or ringing the alarm unit. Alternatively, the output signal of the comparator is supplied also to a timer provided separately, and after the lapse of the set time of the timer the belt conveyor is stopped. In other words, according to this method, if the plastics are admixed in the pulp and papermaking materials or cereals the presence of the plastics is detected by the surface potentiometer from the surface potential thereof and the value is amplified, and when the absolute value exceeds a predetermined value the alarm unit is actuated and the pilot lamp is lighted by the operation of the comparator, and as well the belt conveyor is stopped through the timer after the lapse of a predetermined time. In this case the plastics are removed manually from the pulp and papermaking materials or cereals.

(2) When the presence of plastics is detected by a comparator connected with a potentiometer, a pilot lamp is lighted, an alarm unit rings, then a scraper disposed above a belt conveyor is actuated after some time through a timer so as to automatically remove the pulp and papermaking materials or cereals containing plastics from the conveyor.

(3) A device for removing the mixture of plastics and pulp and papermaking material or cereals is installed at the discharge end of a belt conveyor, and automatically moved in a timely manner to remove that portion of the pulp and papermaking materials containing plastics, then said portion being moved to some other place where the plastics are removed therefrom.

The comparator used in the method of the invention is adapted to set in advance the lower limit (reference value) of the absolute value of the differentiated value of the measured potential and to automatically discriminate whether the measured value is larger than the lower limit or not. Thus, the comparator is a kind of potential comparator.

BRIEF DESCRIPTION OF THE DRAWINGS

FIG. 1 is a schematic vertical sectional view illustrating an example of an apparatus for carrying out the method of the present invention.

FIG. 2 is a schematic lateral sectional view illustrating an example of stationary electrodes for detecting surface potentials in the apparatus in FIG. 1.

FIG. 3 is a circuit diagram showing a circuit arrangement of a potential detector together with signal waveforms of respective units.

FIG. 4 is a lateral sectional view showing a device for removing plastics used in the apparatus.

FIG. 7 is a schematic side view of another example of the apparatus for carrying out the method of the present invention.

FIG. 8 is an explanatory view showing an example of an ionic air generator.

BEST MODE FOR CARRYING OUT THE INVENTION

Figure 5:
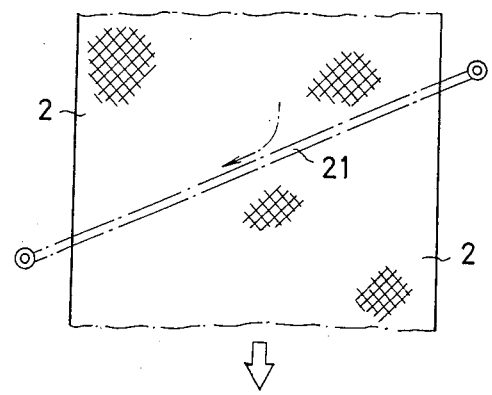
FIG. 5 is a partial plan view of the device.

In order to effectively detect the surface potentials of plastics admixed in pulp and papermaking materials or cereals, it is preferred to spread a thin layer of wood chips or the like and move them on a belt conveyor. The plastics to be detected for their presence by a surface potentiometer include polystyrene, polyethylene, polyvinyl chloride, polycarbonate, polyethylene terephthalate, polytetrafluoroethylene, polypropylene, polyvinylidene chloride, polyvinyl fluoride, polyvinylidene fluoride, epoxy resin, polyacrylic resin, polyamide, melamine resin, polybutadiene, synthetic high molecular compound including copolymer with the same, cellophane, and rubbers, all of which have lower charge attenuating velocity as compared with the pulp and papermaking materials or cereals. The detectable size of the plastics is larger than 1 $mm^2$, but even if particles of the plastics are less than 1 $mm^2$ in size, the plastics having remarkable charging properties such as polystyrene, polyethylene, polypropylene, or polyester can be sufficiently detected by a potentiometer.

Non-wood pulp and papermaking materials such as straw, bagasse, hemp, rag, cotton, linter, or waste paper normally have a lower moisture content than wood chips, and contains less than 5 to 6% by weight. Consequently, even if the non-wood material is corona discharged, a sufficient potential difference may not be obtained between the non-wood pulp and papermaking material and the plastics. Accordingly, when the non-wood pulp and papermaking material is treated, it is preferred to moisten the non-wood pulp and papermaking material at the upstream side of the position of the surface potentiometer (at the upstream side of the position of a discharging bar in the case where corona discharge is employed). For instance, waste paper, newspaper and rag selected as non-wood pulp and papermaking material had moisture contents in the range of 4 to 6% by weight. They were distributed in a thin layer on a conveyor belt having a width of 600 mm and moving at a speed of 8 m/min, and corona discharged by means of electrodes of 10 KV installed at a height of 4 cm above the conveyor belt. Then the surface potentials thereof were measured by means of a surface potentiometer installed at a height of 4 cm above the conveyor belt at positions isolated by 30 cm from the electrodes. Their surface potentials thus measured were −50 to −100 volts. On the other hand, when they were similarly corona discharged after being sprayed with water by means of a shower pipe installed at a height of 40 cm above the conveyor belt so as to adjust their moisture content to a range of 9 to 12% by weight, their surface potentials were only 0 to −2 volts.

Means for moistening the non-wood pulp and papermaking materials is not limited in the invention, but this moistening is generally performed by spraying water over the surfaces of paper or fibers by means of a nozzle shower or the like; moistening by steam is also effective. It is always preferable to adjust the moisture content of the non-wood pulp and papermaking material to within the range of 9 to 60% by weight. In this case, it is also possible to adjust the moisture content after the paper or fibers mixed with the plastics are put on a conveyor belt, and it is rather preferable to moisten the paper or fibers after putting them in a thin layer on the conveyor belt because this ensures relatively uniform moistening adjustment. In this case, the shower pipe is preferably installed at a height of 20 to 50 cm above the conveyor belt to spray water over the paper or fibers.

In carrying out the method of the invention, it is preferable but not indispensable to apply a corona discharge to pulp and papermaking materials or cereals conveyed on a conveyor so as to increase the surface potentials of plastics mixed in with such materials or cereals. Since dusts are frequently adhered to the plastics admixed in the pulp and papermaking materials or cereals, it is effective to perform corona discharging after the pulp and papermaking materials or cereals are supplied to the conveyor through a vibrating screen or a vibrating feeder and, if necessary, the dusts adhered to the plastics are further removed by an air shower, in order to increase the charging potentials of the plastics. When the air shower is employed, the dusts might be charged at a plus potential and adhered to the plastics, and therefore it is desirable to neutralize in advance the charge of the dusts by using ionized air produced by a static eliminating bar. The voltage of the corona discharge is normally in the range of 1 to 50 KV, and it is normal to adjust the distance between the corona discharging bar and the conveyor belt to 3 to 20 cm. The corona discharging bar is a paired electrode made, for example, of stylus electrodes.

The surface potentiometer necessary to carry out the method of the present invention has an amplifier circuit for performing a time differentiating method, it is preferable to position the electrodes as close as possible to the flow of pulp and papermaking material or cereals without contacting the materials. In the case of corona discharge, it is preferable to position the electrodes as near as possible to the discharging position. In this manner, even if the charge on the plastics due to the corona discharge is attenuated, it is possible to detect the difference in surface potential of the plastics from that of the pulp and papermaking materials or cereals. However, it is desirable to ensure that the high voltage of the corona discharge or the increase of the ground potential by spark discharge does not exert an adverse influence, with said close spacing, upon the surface potentiometer or an integrated circuit contained in electronic circuits such as the amplifier circuit or the comparator. It is also possible to use a checking mechanism or circuit to check whether the electronic circuits are in normal operation.

It is preferable that the electrodes of the surface potentiometer are of a bar type because they effectively measure the surface potentials of the plastics moving on the wide belt conveyor, and they normally have a length of a few to 100 cm.

Additionally, since the surface potentiometer employed in the method of the invention has an amplifier circuit for a time differentiating method, the presence of the plastics can be sufficiently detected even when the velocity of the plastics passing under the electrodes is high or when the charging density is small. This is because the charge induced at the electrodes of the surface potentiometer due to the approach of the charge plastics to the electrodes is amplified to a time differentiated value, and the amplified value is outputted to the comparator. Accordingly, in case of a conveyor it is possible to arbitrarily select the moving speed of the conveyor in a range of 1 to 300 m/min.

The present invention will be further described in detail with reference to accompanying drawings.

EXAMPLE 1

As shown in FIG. 1, wood chips contained in a storage unit 1 are continuously dropped onto a belt conveyor 2 of an electrically conductive material through a vibration feeder 3, and flattened so that the chips become a thin layer on the conveyor.

An air shower 4 and stylus corona discharging bars 6 connected to a high voltage power source 5 are provided above the conveying surface of the conveyor 2, whereby dust adhering to the wood chips or to any plastics present is reduced and the wood chip layer is subjected to the corona discharge. Preferably the electrodes of discharging bars comprise a number of styluses buried in bar-shaped insulators. The conductive belt conveyor is grounded as shown in FIG. 1., and is operated at a speed of 50 m/min, for example. The electrode unit 8 of a surface potentiometer 7 having an amplifier circuit is provided in a position about 40 cm behind the bars 6 so as to measure the time differentiated value of the quantity of charge stored on the wood chips as well as the quantity of charge stored on any plastics present.

The bar electrodes $8a$ and $8c$ each having a length of 30 cm are arranged, as shown in FIG. 2, so that each of them shares ⅓ of the width of the belt conveyor 2, and a shielding cover 9 is mounted so as to surround the electrodes. The electrodes $8a$ to $8c$ may be arranged longitudinally in two or three stages. In this manner, the quantity of charge stored on the plastics in the wood chips is detected by the bar electrodes, and the charge is amplified as the time differentiated value by the amplifier circuit of the surface potentiometer 7.

An output amplified by the surface potentiometer 7 is applied to a comparator 10 in FIG. 1, and detected by the comparator as to whether the absolute value thereof is higher than a reference potential.

The above operation will be described in more detail with reference to FIGS. 3. The surface potential detected by the electrodes 8 exhibits a waveform as shown in FIG. 3(a). Since the detected signal is applied to a differentiation type amplifier 7A in the surface potentiometer 7, the waveform becomes a pattern as shown in FIG. 3(b), and is further amplified by a main amplifier 7B in the waveform as shown in FIG. 3(c). Reference symbol 7C represents a sensitivity setting element for defining the amplification factor. The output of the surface potentiometer 7 is applied to the comparator 10 as described above, and an arbitrary reference voltage can be set by suitably adjusting a level setting element 10A in the comparator 10. Stated in other words, the electrodes 8 are connected via resistance with an input terminal of the differentiation type amplifier 7A, which has a feed back resistor connected in parallel therewith. The output current of the amplifier 7A is applied via resistence to the main amplifier 7B, which has the sensitivity setting element 7C. The output current is then applied to the comparator. The reference (lower limit) potential is represented by symbol 10a in FIG. 3(c). Only the signal exceeding the reference potential level is produced as the output of the comparator as shown in FIG. 3(d), and applied to a monostable multi-vibrator 11 of next stage. A time setting element 11A is attached to the monostable multi-vibrator 11 so as to define the operating time of a lamp 12 or an alarm unit 13. The defining time is shown by symbol Δt' in FIG. 3(e).

When the lower limit of potential is, for example, set to −5 volts in the comparator 10 and the absolute value of the signal is detected to be higher than the lower limit of potential, the pilot lamp 12 is energized by the detection signal, or the alarm unit 13 is simultaneously operated. In this case, the reference potential of the comparator and the amplification factor of the amplifier circuit are adjustable according to the magnitude of the detected potential difference.

When the detection signal is produced from the comparator, the presence of the plastics is signalled by the means described above, and a timer 14 separately mounted is operated by the signal and stops a drive drum 2a of the conveyor 2 after the lapse of a predetermined period of time. Subsequently, the plastics admixed in the wood chips on the belt conveyor 2 are manually removed. The present invention thus includes a method of automatically detecting the plastics admixed in the wood chips and manually removing the plastics therefrom.

According to the method of the present invention, the probability of detecting various plastics (polyethylene film, polypropylene (pp) rope, foamed polystyrene, polyvinyl chloride tape, pp straw, polyethylene (PE) dust box broken pieces, polyvinyl chloride sheet, polyester film, polycarbonate, or nylon) present in the wood chips or other conductive substances is higher than about 80%. When the wood chips were passed two or three times through a conveyor equipped with the same plastics detector, the plastics were detected and removed with a probability of more than 95%.

EXAMPLE 2

An example of the invention in which conductive materials containing plastics are automatically partly removed will be described. In the apparatus shown in FIG. 1, a hopper 15 is mounted at the discharge end of the belt conveyor 2, branch tubes 17a, 17b having a damper 16 are arranged at the hopper 15, and the signal of the timer 14 is supplied to an actuator 18 of the damper 16. The damper 16 is normally at the position designated by a broken line in FIG. 1 so that the wood chips or other conductive materials discharged from the conveyor 2 flow through branch tube 17a into a reservoir container 20. When plastics are admixed in the materials, the presence of the plastics is automatically deteced as described above, the timer 14 is operated, and the damper 16 is switched to the position as designated by solid lines in FIG. 1 after the lapse of a predetermined period of time. At this time the materials containing the plastics flow through the branch tube 17b into a plastic container 19. The chips or other conductive materials containing no plastics are supplied to the other container 20 as mentioned above. Thus, automatic sorting is performed.

EXAMPLE 3

Figure 6:
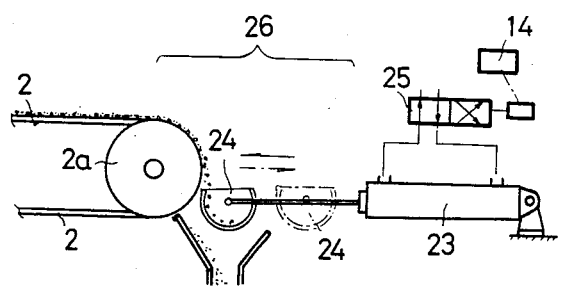
FIG. 6 is a longitudinal sectional view partly illustrating another example of the device for removing the plastics.

As a method of removing plastics admixed in conductive materials, means shown in FIGS. 4 and 5 or FIG. 6 may be adopted. In the arrangement shown in FIGS. 4 and 5, a vertically movable scraper 21 is disposed obliquely in a plan view just above the belt conveyor 2 for conveying the conductive materials, and the changeover valve of an elevation control cylinder 22 is operated by said detection signal and the output signal from the timer 14. The scraper 21 is normally raised as shown by solid lines in FIG. 4, and when the conductive materials admixed with the plastics have arrived at a predetermined position, the scraper 21 is moved downwardly by the above-described signals, thereby the materials being automatically removed as shown by an arrow in FIG. 5.

In the arrangement shown in FIG. 6, a reciprocating plastic container 24 mounted on a piston rod of a cylinder 23 is arranged at the disharge end of the conveyor 2. In this arrangement, a spool valve 25 of a solenoid type is switched via the output signal of the timer 14, causing container 24 to be moved into its forward position (solid lines) to catch the conductive materials admixed with plastics, and the plastics are thereby automatically removed. The entire plastics removing device is generally designated by numeral 26.

EXAMPLE 4

FIG. 7 shows an arrangement in which a plurality of conveyors provided with the detecting means of the invention are disposed in the direction of the conveyance thereof. This arrangement will now be described in detail.

A vibrating screen 31 is arranged at the discharge end of a hopper 30 for wood chips or other electrically conductive materials, and an ionic air generator 32 and an air shower 33 are substantially alternately installed above the screen. Dusts adhering to the wood chips and to any plastics present are removed by the vibration of screen 31. Since the dusts are normally slightly charged positively and are conductive, they are particularly detrimental to the detection of the plastics to be removed, but the dusts are removed before the detection. The air shower 33, as well as the vibrating screen 31, is effective for removing the dusts. In addition, in the arrangement in FIG. 7, the ionic air generator 32 is further installed, and the following advantages are obtained. The generator 23 has paired electrodes 32b in the vicinity of the stylus electrodes 32a of a corona bar as shown in FIG. 8, and is adapted to ionize the air in the environment. The dusts adhered to the wood chips or plastics may be charged positively as mentioned above, and may be electrostatically adhered to the plastics. Even in this case, when ionic air is sprayed through the generator 32, the electrostatic bond is released so as to facilitate the removal of the dusts.

The chips, from which the dusts are thus removed, are introduced to a vibrating feeder 34 in FIG. 7, and a predetermined quantity of chips are supplied in a thin layer onto the next belt conveyor 35. Another conveyor 36 is provided at the discharge end of the belt conveyor 35, automatic switches 37 being respectively provided between the conveyors 35 and 36 and at the discharge end of the conveyor 36. Thus the plastics detected as described below are automatically removed.

Corona discharges 38 are respectively arranged above the conveyors 35 and 36, and the electrodes 39 of surface potentiometer are disposed at the downstream side thereof so that the differences in surface potential are individually detected in the same manner as in Example 1. The treatment after the detection is as already described.

Operating conditions in the above respective examples are listed in the tables below.

surface potentiometer having electrodes disposed above and across the width of said conveying surface, said electrodes being connected via a resistance with an input terminal of a differentiation type amplifier having a feed back resistor connected in parallel therewith, the output current of said amplifier being applied via resistance to a main amplifier having a sensitivity setting element, the output current of said main amplifier being applied to a comparator, inputting said amplified current into said comparator, sending an output signal generated by said comparator to a timer when the voltage of said inputted amplified current exceeds a reference value set in said comparator, and, in response to said output signal received from said comparator, delivering from said timer an output signal according to the set time thereof to effect a subsequent sorting operation.

2. The method as claimed in claim 1, wherein a corona discharge is applied to said thin layer of materials distributed on said conveying surface prior to measuring the surface potential carried on said materials.

3. The method as claimed in claim 1 wherein said

TABLE 3

| Ex. | Conveyor speed (m/min) | Conveyor width (mm) | Distance between bar and conveyor (cm) | Voltage applied to bar (KV) | Interval between bar and electrode (cm) | Number of electrodes | Distance between electrode and the end of conveyor (m) | Distance between electrode and the surface of conveyor (cm) | Time set in timer (sec) | Lower limit value set in comparator (V) |
|---|---|---|---|---|---|---|---|---|---|---|
| 1 | 50 | 300 | 5 | 7 | 40 | 1 | 2 | 5 | 2.4 | −5 |
| 2 | 50 | 600 | 5 | 10 | 40 | 2 | 2 | 5 | 2.4 | −5 |
| 3 | 50 | 900 | 5 | 10 | 40 | 3 | 2 | 5 | 2.4 | −5 |

OPERATING CONDITIONS OF EXAMPLE 4

Applied voltage of ionic air generator: 7 KV
Spraying rate of air shower: 200 liters/min
Vibrating screen: Model RVS-450 made by Shinko Electric Co., Ltd. (Capacity: Max. 0.14 m³/min)
Vibrating feeder: Model F-22BDT made by Shinko Electric Co., Ltd. (Capacity: Max. 0.12 m³/min)

materials distributed on said conveying surface are subject to a dust removing operation prior to measuring the surface potential carried on said materials.

4. The method as claimed in claim 3 wherein said materials are subjected to a vibrating feeder.

5. The method as claimed in claim 3 wherein said materials are subjected to an air shower.

6. The method as claimed in claim 3 wherein said

TABLE 4

| | Conveyor speed (m/min) | Conveyor width (cm) | Feeding rate (m³/min) | Applied voltage of corona discharge (KV) | Corona discharger (Linear type) | Distance between bar and conveyor (cm) |
|---|---|---|---|---|---|---|
| Front belt conveyor | 80 | 60 | 0.08 | 11 | one, 5 row | 5 |
| Rear belt conveyor | 80 | 60 | 0.08 | 11 | one, 5 row | 5 |

| | Distance between bar and electrode (cm) | Number of electrodes | Distance between electrode and the end of conveyor (cm) | Distance between electrode and the surface of conveyor (cm) | Time set in timer (sec) | Lower limit value set in comparator (V) |
|---|---|---|---|---|---|---|
| Front belt conveyor | 80 | 2 | 130 | 5 | 1 | −5 |
| Rear belt conveyor | 80 | 2 | 130 | 5 | 1 | −5 |

The conveyor belts in the various examples are of an electrically conductive material.

What is claimed is:

1. A method of detecting and sorting pieces of insulating material admixed in small pieces of conductive material which comprises distributing said material in a thin layer on an electrically conductive surface, conveying said materials forward on said conveying surface, measuring the value proportional to the change of surface charge carried on said materials by means of a materials are subjected to an ionic air shower.

7. The method as claimed in claim 1 wherein said insulating material is a plastic and said conductive material is one from the group consisting of pulp and paper-making materials and cereals.

8. A method of detecting and sorting pieces of insulating material admixed in small pieces of conductive material which comprises distributing said materials in a thin layer on an electrically conductive conveying surface, conveying said materials forward on said conveying surface, measuring the value proportional to the change of surface charge carried on said materials by means of a surface potentiometer having electrodes disposed above and across the width of said conveying surface, said electrodes being connected via a resistance with an input terminal of a differentiation type amplifier having a feed back resistor connected in parallel therewith, the output current of said amplifier being applied via resistance to a main amplifier having a sensitivity setting element, the output current of said main amplifier being applied to a comparator, inputting said amplified current into said comparator, sending an output signal generated by said comparator to a timer when the voltage of said inputted amplified current exceeds a reference value set in said comparator, and, in response to said output signal received from said comparator, delivering from said timer an output signal according to the set time thereof to cause the movement of the conveying surface to stop for sorting.

9. A method of detecting and sorting pieces of insulating material admixed in small pieces of conductive material which comprises distributing said materials in a thin layer on an electrically conductive conveying surface, conveying said materials forward on said conveying surface, measuring the value proportional to the change of surface charge carried on said materials by means of a surface potentiometer having electrodes disposed above and across the width of said conveying surface, said electrodes being connected via a resistance with an input terminal of a differentiation type amplifier having a feed back resistor connected in parallel therewith, the output current of said amplifier being applied via resistance to a main amplifier having a sensitivity setting element, the output current of said main amplifier being applied to a comparator, inputting said amplified current into said comparator, sending an output signal generator by said comparator to a timer when the voltage of said inputted amplified current exceeds a reference value set in said comparator, and, in response to said output signal received from said comparator, delivering from said timer an output signal according to the set time thereof to cause said materials to be selectively discharged from said conveying surface.

* * * * *